United States Patent [19]

Ishii et al.

[11] Patent Number: 4,649,199
[45] Date of Patent: Mar. 10, 1987

[54] SALT OF DC-52 AND A PHARMACEUTICAL COMPOSITION CONTAINING THE SAME

[75] Inventors: Shinzo Ishii, Hofu; Shigeo Katsumata, Mishima; Yukou Arai, Susono; Kazuhisa Fujimoto; Makoto Morimoto, both of Shizuoka, all of Japan

[73] Assignee: Kyowa Hakko Kogyo Co., Ltd., Tokyo, Japan

[21] Appl. No.: 697,918

[22] Filed: Feb. 4, 1985

[30] Foreign Application Priority Data

Mar. 16, 1984 [JP] Japan .................................. 59-51578

[51] Int. Cl.$^4$ .................... A61K 31/495; C07D 498/22
[52] U.S. Cl. ..................................................... 544/342
[58] Field of Search ........................ 514/250; 544/342

[56] References Cited

FOREIGN PATENT DOCUMENTS 0128370 12/1984 European Pat. Off. .
170189 10/1982 Japan .

OTHER PUBLICATIONS

Kyowa et al., Chem. Abs., 98, 87622 (1982).
Hirata et al., Chem. Abs., 102, 203808 (12-19-84).
Kyowa, Chemical Abstracts, vol. 98, 1983, p. 416, No. 87622z.
Takahashi, Chemical Abstracts, vol. 99, 1983, p. 324, No. 101979a.
Takahashi, J. Antibiot., 36, 468–70 (1983).
Tomita, Chemical Abstracts, vol. 99, 1983, p. 474, No. 68776g.
Tomita, J. Antibiotics, 1983, 36, 463–67.

Primary Examiner—Mark L. Berch
Attorney, Agent, or Firm—Fitzpatrick, Cella, Harper & Scinto

[57] ABSTRACT

A pharmacologically acceptable acid addition salt of DC-52 with 0.5–2.0 equivalent weight of inorganic acid, sulfonic acid, acidic amino acid, citric acid, transaconitic acid, α-ketoglutaric acid, itaconic acid, malonic acid or ascorbic acid on the basis of DC-52, having the same degree of antitumor activity as DC-52, is superior to DC-52 in stability at powdering or at preservation.

4 Claims, 8 Drawing Figures

SALT OF DC-52 AND A PHARMACEUTICAL COMPOSITION CONTAINING THE SAME

TECHNICAL FIELD

This invention relates to a salt of DC-52 and a pharmaceutical composition containing the same. The salt has an antitumor activity.

BACKGROUND ART

DC-52 is a substance produced by *Streptomyces melanovinaceus* DO-52, FERM BP-654, which was transferred on Nov. 12, 1984 from FERM P-5911 deposited on Mar. 14, 1981, and has the following structure and an antitumor activity upon leukemia P-388 ascites type tumor cells (Japanese Published Unexamined Patent Application No. 170189/1982).

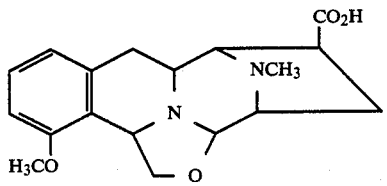

However, DC-52 is unstable and liable to decompose during the purification and powdering (for example, freeze-drying), and DC-52 of high purity can not be obtained. The decomposition proceeds even during the preservation.

DISCLOSURE OF THE INVENTION

The stability of DC-52 in an aqueous solution against pH was measured, and it was found, as shown in Table 1 that the stability was a little improved at pH 5–6, but extremely lowered when a half equivalent weight or equal equivalent weight of hydrochloric acid was added thereto on the basis of DC-52 to make pH below 4.

TABLE 1

| pH | Hydrochloric acid[*1] | Stability (%)[*2] 50° C., one day | 50° C., two days |
|---|---|---|---|
| 7.5 | 0 | 61.1 | 32.6 |
| 6.0 | 0.05 | 66.9 | 37.8 |
| 5.0 | 0.10 | 63.2 | 35.4 |
| 4.0 | 0.15 | 48.6 | 29.6 |
| 3.0 | 0.5 | 46.2 | 27.4 |
| 2.5 | 1.0 | 40.1 | 22.8 |
| 2.2 | 1.5 | 32.4 | 19.9 |
| 2.1 | 2.0 | 30.1 | 17.8 |

[*1]equivalent weight on the basis of DC-52, where one mole of DC-52 was presumed to be 2 equivalent weights
[*2]value just after the preparation Analysis of DC-52 was made by subjecting 10 μl each of solutions adjusted to a concentration of 1,000 μg/ml in terms of DC-52 to a high performance liquid chromatography (measuring wavelength: 271 nm) using Nucleodyl 10C18 (made by Gas-chro Kogyo Co., Japan) as a filler, and acetonitrile: 0.1M phosphate buffer (pH 7.0)=1:9 as a moving phase.

Thus, it was presumed that the stability of DC-52 hydrochloride was poorer than that of DC-52, and that an improvement of the stability by salts of DC-52 was difficult. However, contrary to the expectatations, it was found that powder with a very high purity could be obtained when an aqueous solution of DC-52 hydrochloride was immediately freeze-dried and powdered and when its purity was measured, as shown in Table 2.

TABLE 2

| Hydrochloric acid[*1] | Purity[*2] of powder with freeze-drying (%) | pH[*3] |
|---|---|---|
| 0 | 87.0 | 7.5 |
| 0.2 | 89.0 | 3.8 |
| 0.5 | 98.5 | 3.1 |
| 1.0 | 98.3 | 2.9 |
| 1.5 | 98.1 | 2.8 |
| 2.0 | 98.3 | 2.7 |

[*1]equivalent weight on the basis of DC-52
[*2]Analysis of DC-52 was made by subjecting each powder to a high performance liquid chromatography under the same conditions as in the annotation of Table 1.
[*3]pH when the powder was made into an aqueous solution at a concentration of 1,000 μg/ml.

That is, the stability of hydrochloride at freeze-drying was remarkably improved.

Thus, salts with other acids were likewise investigated, and it was found that the stability depended upon the species of acids, and most of salts having a good stability at freeze-drying could often have a good stability at preservation, and further that the stability also depended upon the equivalent weight of acid in the salt on the basis of DC-52, as in the case of the hydrochloride.

Thus, this invention relates to a salt of DC-52, and more particularly to a pharmacologically acceptable acid addition salt of DC-52 with 0.5–2.0 equivalent weight of inorganic acid, sulfonic acid, acidic amino acid, citric acid, trans-aconitic acid, α-ketoglutaric acid, itaconic acid, malonic acid or ascorbic acid.

As apparent from the above statement, the present invention is based on various novel findings that the stability in an aqueous solution of a specific acid addition salt of DC-52, and the stability at powdering or at preservation are different from each other, the stability depends upon the equivalent weight of an acid in an acid addition salt on the basis of DC-52, etc., and the present invention does not relate to mere acid addition salts.

The various salts of DC-52 according to the present invention have antitumor activities almost equal to DC-52 upon leukemia P-388, Xenograft MX1, etc., Sarcoma 180 solid tumor, Lewis lung carcinoma solid tumor, Hela $S_3$, L1210, melanoma B16 and ovarian carcinoma M5076.

Among the acids for use in the present invention, the inorganic acid includes hydrochloric acid, hydrobromic acid, hydroiodic acid, sulfuric acid, nitric acid, phosphoric acid, etc.; the sulfonic acid includes methanesulfonic acid, ethanesulfonic acid, propanesulfonic acid, methanedisulfonic acid, α, β-ethanedisulfonic acid, benzenesulfonic acid, p-toluenesulfonic acid, etc.; and the acidic amino acid includes glutamic acid, aspartic acid, etc. In order to maintain a high stability of acid addition salts of DC-52 according to the present invention, it is necessary that a ratio of the acid to DC-52 in the acid addition salts by equivalent weight is 0.5–2.0, where one mole of DC-52 is presumed to be 2 equivalent weight, and preferably substantially 1.0.

Furthermore, it is preferable that the present acid addition salt is in a powdery state, and a powdering procedure is not particularly limited, but freeze-drying is preferable.

The present acid addition salt of DC-52 can be obtained by reacting DC-52 with a predetermined amount of a suitable acid in an aqueous solution according to the ordinary process, followed by concentration and drying or by freeze-drying. Purification operation such as recrystallization, etc. can further be carried out after the reaction.

DC-52 can be obtained according to a process disclosed in Japanese Published Unexamined Patent Application No. 170189/1982. That is, a DC-52 producing strain *Streptomyces melanovinaceus* DO-52 is inoculated in a medium prepared by properly combining a carbon source such as glucose, fructose, sucrose, starch, etc.; a nitrogen source such as ammonium sulfate, ammonium chloride, urea, peptone, meat extract, yeast extract, corn steep liquor, soybean meal, etc.; an inorganic salt such as sodium chloride, potassium chloride, magnesium sulfate, calcium carbonate, potassium phosphate, manganese sulfate, zinc sulfate, etc.; vitamins, etc., and is subjected to liquid culturing. Usually, by culturing for 1-7 days at a culture liquor temperature of 25°-40° C. and pH 4-10, DC-52 is accumulated in the culture liquor and within the cells. The cells are separated from the culture liquor after the culturing, and the culture liquor is passed through a column filled with a porous resin. Then, the adsorbed substance is eluted therefrom with methanol, acetone, ethyl acetate, etc. The eluate is concentrated, the residue is absorbed onto celite powder, and DC-52 is eluted therefrom with methanol, acetone, etc. and further purified through a combination of solvent extraction, distribution chromatography, etc.

According to a further feature of the present invention, there is provided a pharmaceutical composition, comprising as active ingredient at least one salt of DC-52 as hereinbefore defined in association with a physiologically acceptable carrier or excipient. The composition can be used for treating tumor of mammals, especially human being. The carrier or excipient may take various forms depending upon the desired formulation. Thus, for example, one or more salts of DC-52 as hereinbefore defined may, for example, be dissolved in a physiological solution of sodium chloride, or a solution of glucose, lactose and/or mannitol in order to formulate a pharmaceutical composition suitable for injection.

Alternatively, it is possible to freeze-dry the compounds or compound of the present invention, to which sodium chloride is added to prepare a powderly injection agent. The composition may, if desired, comprise conventional additives or excipients such as pharmaceutically acceptable salts which are well known in the pharmaceutical art. The dosage units may contain any appropriate amount of active ingredient, for example, an amount of 0.02 to 1 mg/kg/day, although the daily dose may vary with differing conditions. The administration may be effected, for example, by intravenous injection and may be administered, for example, from 1 to 3 times per week. The present invention thus includes compositions of the present invention in sterile form.

If desired, oral administration may be possible. Dosage unit forms suitable for oral administration may, for example, include tablets, powders, granules and ampoules and may further contain appropriate excipients well known in the pharmaceutical art. If desired, the composition may be administered, for example, into the artery, abdominal cavity or thorax.

Examples of the present invention will be given below.

EXAMPLE 1

*Streptomyces melanovinaceus* DO-52 as a seed strain is inoculated in 300 ml of a first seed medium (40 g/l KCl, 0.5 g/l $MgSO_4.7H_2O$, 1.5 g/l $KH_2PO_4$, 5.0 g/l ammonium sulfate, 20 g/l sucrose, 10 g/l fructose, 10 g/l glucose, 5.0 g/l corn steep liquor, 20 g/l $CaCO_3$, pH 7.0) in a 2 l-Erlenmeyer flask and cultured at 30° C. with shaking (220 rpm) for 48 hours. Then, 1,500 ml of the thus obtained first seed culture liquor is added to 100 l of a second seed medium having the same composition as that of the first seed medium in a 200 l-fermenter and cultured at 30° C. with aeration and stirring (150 rpm; aeration rate 70 l/min) for 48 hours. Then, 100 l of the thus obtained second seed culture liquor is added to 1 kl of a fermentation medium (50 g/l glucose, 0.3 g/l $KH_2PO_4$, 0.4 g/l $K_2HPO_4$, 0.2 g/l $MgSO_4.7H_2O$, 20 g/l soybean cake powder, 1 g/l $CaCO_3$, pH 7.0) in a 2 kl-fermenter and cultured at 30° C. with aeration and stirring (150 rpm; aeration rate 200 l/min) for 72 hours. After the completion of culturing, 50 μg/ml DC-52 is accumulated in the culture liquor.

A filter aid is added to the culture liquor, and the cells are removed therefrom by filtration, whereby 1.1 kl of culture filtrate is obtained. The culture filtrate is passed through a column filled with 50 l of a porous absorbing resin Diaion HP-10 (trademark of Mitsubishi Kasei Kogyo Co., Ltd., Japan) to absorb DC-52 onto the resin. After the absorption, the resin is washed with water, and eluted with a 6% aqueous acetone. The eluate is concentrated under reduced pressure to obtain 10 l of a concentrated solution. Then, 40 l of ethanol is added to the cncentrated solution to precipitate the impurities, and the mixture is subjected to centrifugation to obtain a supernatant. The supernatant is concentrated under reduced pressure, and a solution of ethanol:water=15:1 is added thereto to prepare a silica gel charge solution.

The charge solution is passed through a column of 10 l of silica gel (100-200 meshes made by Kanto Kagaku Co., Japan) filled with an eluting agent of ethanol:water=15:1, and then developed with the eluting agent, whereby DC-52 is eluted between 4-fold and 6-fold volumes on the basis of the resin volume. Fractions containing the DC-52 are joined together, and concentrated under reduced pressure. Then, water is added to the concentrate, and the mixture is again concentrated to remove ethanol therefrom. The concentrate is filtered through a millipore filter (pore size 0.45μ) to remove turbidity-forming substances therefrom and obtain 250 ml of a filtrate with a DC-52 concentration of 42 g/l. Then, 10 ml of the filtrate is cooled to 5° C., adjusted to pH 2.8 with hydrochloric acid, and freeze-dried to obtain 508 mg of DC-52 hydrochloride powder [equivalent weight ratio: 0.90 (ratio of hydrochloric acid to DC-52 by equivalent weight)].

Melting point: 160°-180° C.

Ultraviolet absorption spectrum: FIG. 1.

Infrared absorption spectrum; (KBr tablet method): FIG. 2.

EXAMPLE 2

In this example, 10 ml of the DC-52 millipore filtrate obtained in Example 1 is cooled to 5° C., adjusted to pH 2.7 with phosphoric acid, and then freeze-dried to obtain 524 mg of DC-52 phosphate powder (equivalent weight ratio: 0.90)

Melting point: 128°-132° C.

Ultraviolet absorption spectrum: FIG. 7.
Infrared absorption spectrum; (KBr tablet method): FIG. 8.

EXAMPLE 3

In this example, 10 ml of the DC-52 millipore filtrate obtained in Example 1 is cooled to 5° C., admixed with 224 mg of ascorbic acid, and then freeze-dried to obtain 705 mg of DC-52 ascorbate powder (equivalent weight ratio: 0.50).

Melting point: 129°–132° C.
Ultraviolet absorption spectrum: FIG. 3.
Infrared absorption spectrum; (KBr tablet method): FIG. 4.

EXAMPLE 4

In this example, 10 ml of the DC-52 millipore filtrate obtained in Example 1 is cooled to 5° C., adjusted to pH 3.0 with citric acid, and then freeze-dried to obtain 630 mg of DC-52 citrate powder (equivalent weight ratio: 1.1).

Melting point: 105°–150° C.
Ultraviolet absorption spectrum: FIG. 5.
Infrared absorption spectrum; (KBr tablet method): FIG. 6.

EXAMPLE 5

Salts of DC-52 with various acids obtained in the same manner as in Examples 1–4 (ratio of acid to DC-52 by equivalent weight=1:1) (freeze-dried products) are analyzed by a high performance liquid chromatography [filler: Nucleodyl 10C18; developing solvent=acetonitrile: 0.1M phosphate buffer (pH 7.0)=1:9] just after preparation and after preservation in vacuum-stoppered ampoules for 60 days in a thermostat at 30° C. The results are shown in Table 3.

It is apparent from Table 3 that the present acid addition salts have a good stability at powdering and also a good stability mostly after preservation.

TABLE 3

| Species of DC-52 salts | Powder purity (%) | pH*1 | Remaining activity after preservation (%) |
|---|---|---|---|
| Hydrochloride | 98.4 | 2.9 | 95.0 |
| Sulfate | 98.5 | 2.7 | 93.1 |
| Phosphate | 98.5 | 2.8 | 98.3 |
| Nitrate | 98.6 | 2.7 | 94.7 |
| Methanesulfonate | 98.5 | 2.9 | 97.4 |
| Benzenesulfonate | 98.3 | 2.9 | 97.0 |
| p-Toluenesulfonate | 98.3 | 2.9 | 96.5 |
| Citrate | 99.5 | 3.2 | 99.0 |
| Trans-aconate | 99.2 | 3.2 | 98.5 |
| α-Ketoglutarate | 98.4 | 3.4 | 94.8 |
| Itaconate | 98.0 | 3.4 | 79.8 |
| Malonate | 98.0 | 3.3 | 79.9 |
| Ascorbate | 99.0 | 3.8 | 96.5 |
| Glutamate | 98.5 | 4.0 | 91.4 |
| Aspartate | 98.0 | 4.0 | 98.5 |
| Acetate | 89.0 | 4.4 | 70.4 |
| Oxalate | 92.0 | 3.0 | 97.0 |
| Succinate | 95.0 | 3.4 | 84.1 |
| Glutarate | 93.0 | 3.6 | 76.5 |
| Propionate | 92.0 | 3.9 | 83.5 |
| Lactate | 96.0 | 3.6 | 90.0 |
| DC-52 | 87.5 | 7.0 | 76.4 |

*1 pH when the powder just after preparation was made into an aqueous solution at a concentration of 1,000 μg/ml.

EXAMPLE 6

DC-52 citrates in various equivalent weight ratios are prepared according to the same manner as in Examples 1–4, and purity, pH and remaining activity after preservation are investigated in the same manner as in Example 5. The results are shown in Table 4.

TABLE 4

| Citrate equivalent weight ratio | Powder purity (%) | pH | Remaining activity after preservation (%) |
|---|---|---|---|
| 0 | 87.0 | 7.3 | 77.6 |
| 0.6 | 98.2 | 3.7 | 96.4 |
| 1.0 | 99.1 | 3.5 | 99.4 |
| 1.5 | 98.9 | 3.3 | 94.5 |

EXAMPLE 7

Antitumor activity

A cell suspension of $5 \times 10^6$/ml of leukemia P-388 cells maintained intraperitoneally in DBA/2 male mouse is prepared with sterilized physiological saline solution. Then, 0.2 ml of the cell suspension is inoculated intraperitoneally into groups of mice, each group consisting of 5 $CDF_1$ male mice, each having a body weight of about 25 g. DC-52, DC-52 hydrochloride, and DC-52 citrate are administered intraperitoneally at dosages given in Table 5, with three injections, on day 1, day 5 and day 9 after the tumor inoculation.

The results are shown in Table 5, where an antitumor effect is represented in T/C %, percentage of average survival days (T) of the administered group to average survival days (C) of the non-administered group.

TABLE 5

| Administration (mg/kg/day) | T/C (%) DC-52 hydrochloride | T/C (%) DC-52 citrate | T/C (%) DC-52 |
|---|---|---|---|
| 6.25 | 154 | 157 | 161 |
| 3.13 | 143 | 137 | 158 |
| 1.56 | 124 | 126 | 116 |

It can be said from the above table that antitumor activities of the three compounds are substantially equal.

EXAMPLE 8

Antitumor activity after preservation

The procedure described in Example 7 is repeated using each compound in Table 6, except that the compound is administered once a day for 7 days from day 1 after tumor inoculation.

The results are shown in Table 6.

TABLE 6

| Administration (mg/kg/day) | T/C (%) DC-52 hydrochloride | T/C (%) DC-52 citrate | T/C (%) DC-52 | Preservative condition of test compound |
|---|---|---|---|---|
| 12.5 | toxic | toxic | toxic | before preservation |
| 9.38 | 183 | 194 | 198 | |
| 6.25 | 150 | 160 | 155 | |
| 3.13 | 139 | 132 | 141 | |
| 1.56 | 110 | 124 | 117 | |
| 12.5 | toxic | toxic | 165 | after preservation for 3 months at 30° C. |
| 9.38 | 195 | 203 | 150 | |
| 6.25 | 167 | 161 | 139 | |
| 3.13 | 133 | 140 | 125 | |
| 1.56 | 120 | 117 | 111 | |

It is apparent from Table 6 that antitumor activities of DC-52 hydrochloride and DC-52 citrate do not deteriorate after preservation, being different in case of DC-52.

EXAMPLE 9

Acute toxicity ($LD_{50}$)

As test animals, ddY male mice, one group consisting of 5 mice, are used. DC-52 citrate is intraperitoneally administered once to the mouse, and the death ratio of the animals is observed for 14 days, from which $LD_{50}$ is calculated by Behrems-Korber's method to be 21.6 mg/kg.

EXAMPLE 10

In this example, 5 g of DC-52 citrate is dissolved in 1000 ml of ethanol and sterilized by filtering under pressure by the use of Millipore Filter (commercial product of Millipore Corpn., U.S.A.) having a pore size of $0.22\mu$. Then, 1.0 ml of the resultant sterilized filtrate is poured into brown vials (10 mg/vial) and frozen at $-50°$ C. for 2 hours. After confirming that the temperature of the ingredient in the vial reaches the atmospheric temperature, the material is further dried in vacuo under 0.1 mmHg at an atmospheric temperature of 20° C. for 4 hours, and the vial is sealed with a rubber plug. In use, a sterilized physiological sodium chloride solution (5 ml) containing a dissolution aid is added to the ingredient and well stirred to obtain an injection solution.

EXAMPLE 11

In this example, 10 mg of DC-52 citrate, 90 mg of lactose, 40 mg of corn starch, 4 mg of polyvinyl alcohol, 28 mg of Avicel (microcrystalline cellulose commercially available from FMC Corpn., U.S.A.) and 1 g of magnesium stearate are used to prepare a tablet in conventional manner.

Figure 1:
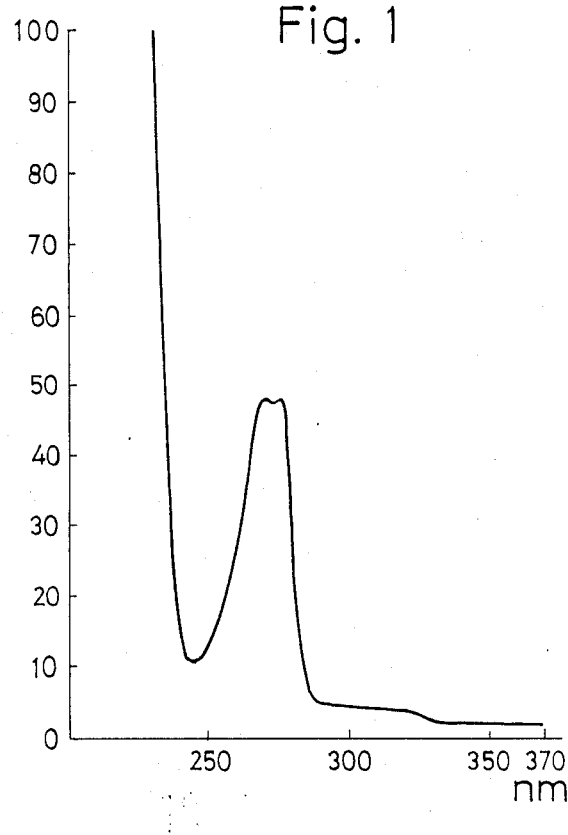
FIGS. 1, 3, 5 and 7 show ultraviolet absorption spectra of DC-52 hydrochloride, DC-52 ascorbate, DC-52 citrate and DC-52 phosphate, respectively.
Figure 2:
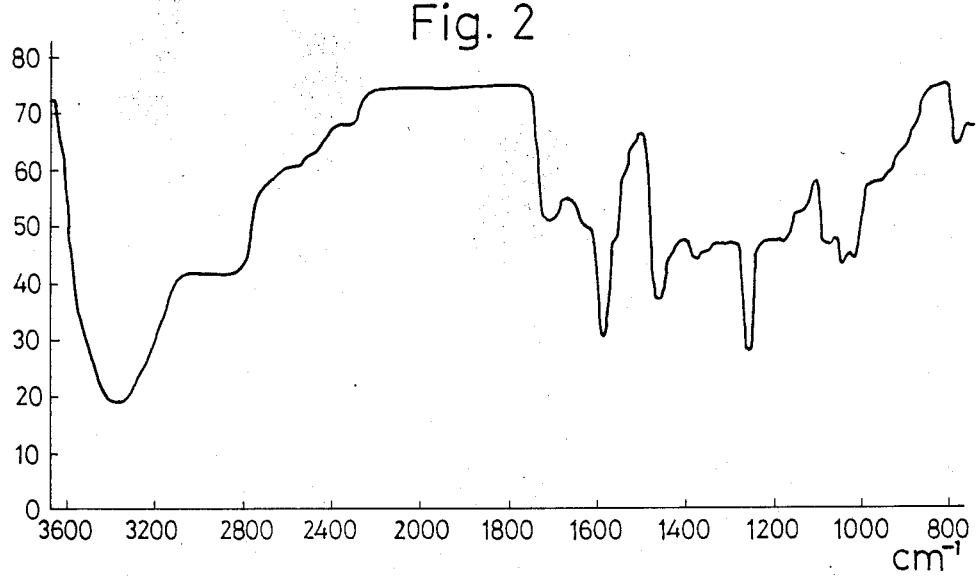
FIGS. 2, 4, 6 and 8 show infrared absorption spectra of DC-52 hydrochloride, DC-52 ascorbate, DC-52 citrate and DC-52 phosphate, respectively.
Figure 3:
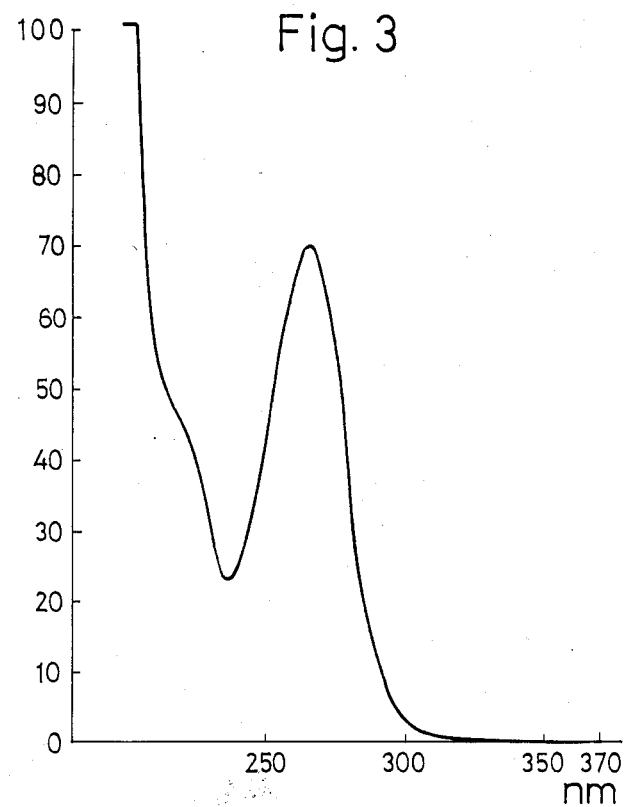
Figure 4:
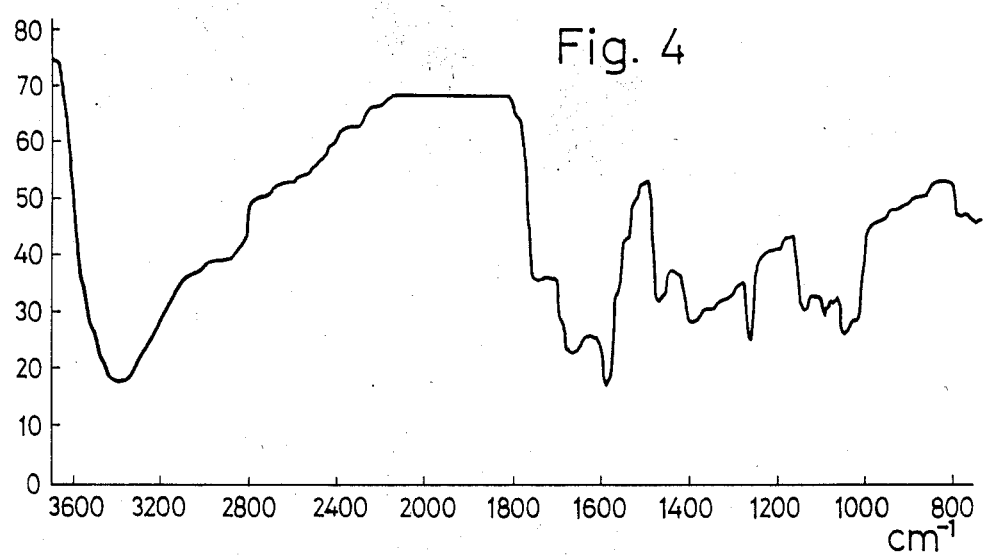
Figure 5:
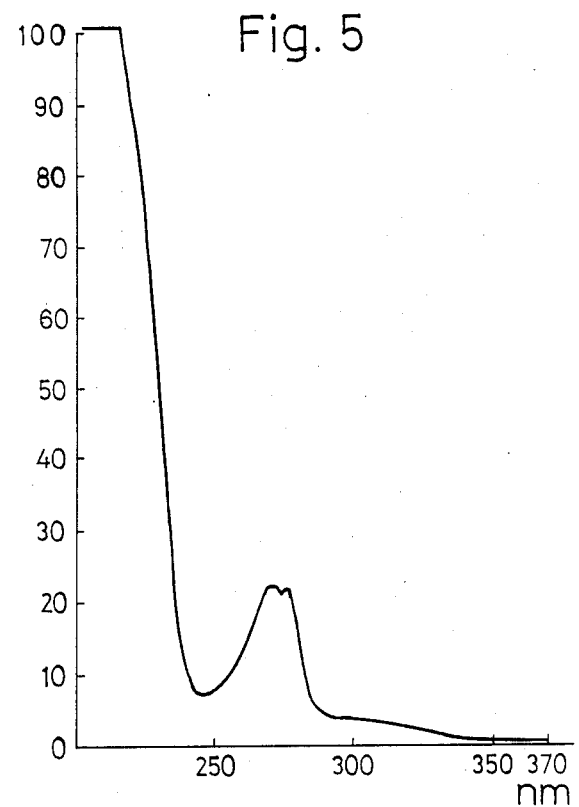
Figure 6:
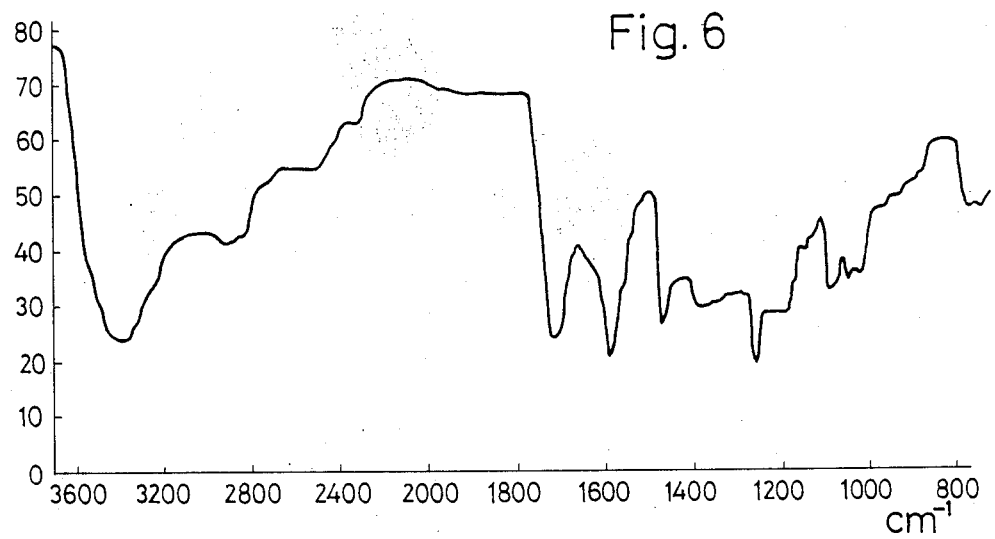
Figure 7:
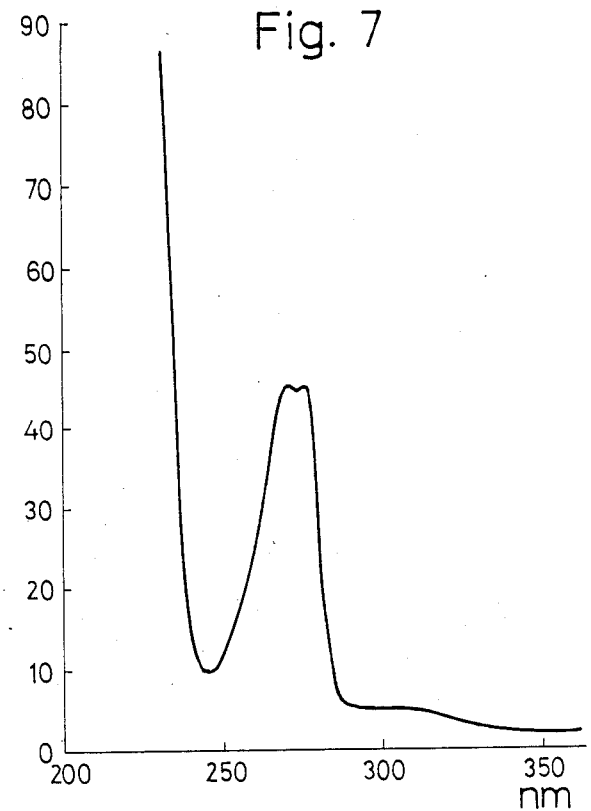
Figure 8:
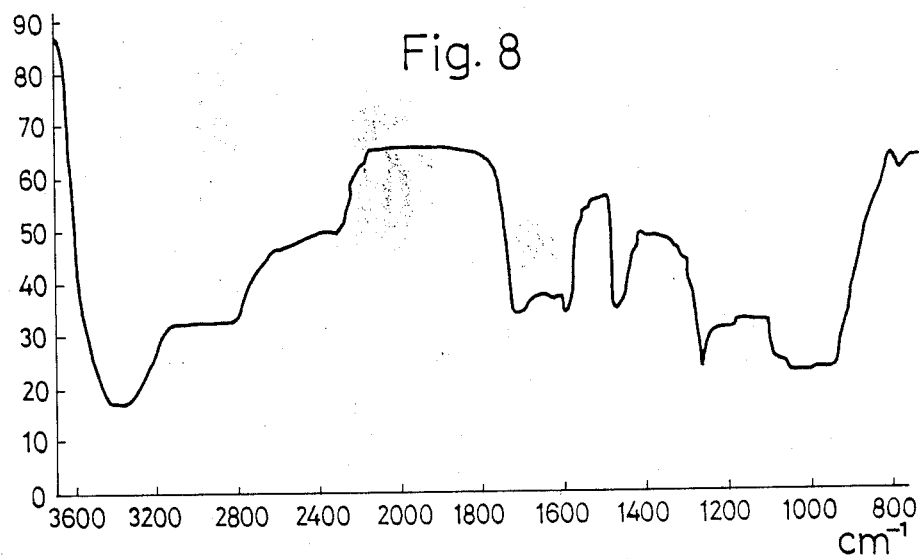

What is claimed is:

1. A pharmacologically acceptable acid addition salt in a powdery state of a compound represented by the formula:

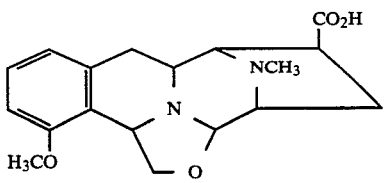

(hereinafter referred to as DC-52) with 0.5–2.0 equivalent weight of inorganic acid, sulfonic acid, acidic amino acid, citric acid, trans-aconitic acid, $\alpha$-ketoglutaric acid, itaconic acid, malonic acid or ascorbic acid on the basis of DC-52.

2. An acid solution salt according to claim 1, wherein the inorganic acid is hydrochloric acid, hydrobromic acid, hydroiodic acid, sulfuric acid, nitric acid or phosphoric acid; the sulfonic acid is methanesulfonic acid, ethanesulfonic acid, propanesulfonic acid, methanedisulfonic acid, $\alpha$, $\beta$-ethanedisulfonic acid, benzensulfonic acid or p-toluenesulfonic acid; and the acidic amino acid is glutamic acid or aspartic acid.

3. An acid addition salt according to claims 1 or 2 wherein an amount of the acid to be used is one equivalent weight on the basis of DC-52.

4. An acid addition salt according to claims 1 or 2 wherein the acid addition salt is a freeze-dried product.

* * * * *